(12) United States Patent
Al-Ghrami et al.

(10) Patent No.: US 9,605,213 B2
(45) Date of Patent: Mar. 28, 2017

(54) METHOD FOR THE FLUIDIZED CATALYTIC CRACKING OF A HEAVY HYDROCARBON FEEDSTOCK

(71) Applicants: Saudi Arabian Oil Company, Dhahran (SA); King Fahd University of Petroleum and Minerals, Dhahran (SA)

(72) Inventors: Musaed Salem Al-Ghrami, Dhahran (SA); Cemal Ercan, Dhahran (SA); Sulaiman S. Al-Khattaf, Dhahran (SA); Mohammed Abdul Bari Siddiqui, Dhahran (SA); Abdullah M. Aitani, Al-Khobar (SA)

(73) Assignees: SAUDI ARABIAN OIL COMPANY (SA); KING FAHD UNIVERSITY OF PETROLEUM AND MINERALS (SA)

( * ) Notice: Subject to any disclaimer, the term of this patent is extended or adjusted under 35 U.S.C. 154(b) by 0 days.

(21) Appl. No.: 15/015,448

(22) Filed: Feb. 4, 2016

(65) Prior Publication Data
US 2016/0152900 A1 Jun. 2, 2016

Related U.S. Application Data

(63) Continuation of application No. 13/900,725, filed on May 23, 2013, now Pat. No. 9,284,492.

(60) Provisional application No. 61/652,019, filed on May 25, 2012.

(51) Int. Cl.
| | |
|---|---|
| *C10G 11/05* | (2006.01) |
| *C07C 4/06* | (2006.01) |
| *B01J 29/80* | (2006.01) |
| *B01J 38/00* | (2006.01) |
| *B01J 38/02* | (2006.01) |
| *B01J 29/08* | (2006.01) |
| *B01J 29/40* | (2006.01) |
| *B01J 29/90* | (2006.01) |
| *B01J 35/02* | (2006.01) |
| *C10G 11/18* | (2006.01) |
| *B01J 35/00* | (2006.01) |
| *B01J 21/16* | (2006.01) |
| *B01J 37/28* | (2006.01) |

(52) U.S. Cl.
CPC .............. *C10G 11/05* (2013.01); *B01J 21/16* (2013.01); *B01J 29/084* (2013.01); *B01J 29/40* (2013.01); *B01J 29/80* (2013.01); *B01J 29/90* (2013.01); *B01J 35/0006* (2013.01); *B01J 35/023* (2013.01); *B01J 38/00* (2013.01); *B01J 38/02* (2013.01); *C07C 4/06* (2013.01); *C10G 11/18* (2013.01); *C10G 11/182* (2013.01); *B01J 37/28* (2013.01); *B01J 2229/186* (2013.01); *B01J 2229/24* (2013.01); *C10G 2400/02* (2013.01); *C10G 2400/20* (2013.01)

(58) Field of Classification Search
USPC .............................. 208/114, 120.01; 585/653
See application file for complete search history.

(56) References Cited

U.S. PATENT DOCUMENTS

| | | |
|---|---|---|
| 3,074,878 A | 1/1963 | Pappas |
| 3,758,403 A | 9/1973 | Rosinski |
| 3,894,931 A | 7/1975 | Nace et al. |
| 3,894,934 A | 7/1975 | Owen et al. |
| 4,309,280 A | 1/1982 | Rosinski et al. |

(Continued)

FOREIGN PATENT DOCUMENTS

| | | |
|---|---|---|
| AU | 2011202519 | 6/2011 |
| EP | 0020154 | 12/1980 |
| EP | 0909582 | 4/1999 |

OTHER PUBLICATIONS

Gao, X., et al., Influence of Particle Size of ZSM-5 on the yield of Propylene in Fluid Catalytic Cracking Reaction; Journal of Molecular Catalysis A: Chemical; Jun. 15, 2010; pp. 36-39; vol. 325, No. 1-2; Elsevier B.v.; www.elsevier.com/locate/molcata.

(Continued)

*Primary Examiner* — Elizabeth Wood
(74) *Attorney, Agent, or Firm* — Bracewell LLP; Constance Gall Rhebergen

(57) ABSTRACT

Embodiments of the invention provide a method for the fluid catalytic cracking of a heavy hydrocarbon feedstock. According to at least one embodiment, the method includes supplying the heavy hydrocarbon feedstock to a reaction zone having a catalyst, such that both the heavy hydrocarbon feedstock and the catalyst are in contact in a down-flow mode, wherein said contact between the heavy hydrocarbon feedstock and the catalyst takes place in a fluidized catalytic cracking apparatus having a separation zone, a stripping zone, and a regeneration zone. The method further includes maintaining the reaction zone at a temperature of between 500 and 600° C., such that the hydrocarbon feedstock converts into a cracked hydrocarbon effluent comprising light olefins, gasoline, and diesel. The catalyst includes between 10 and 20% by weight of a phosphorous modified sub-micron ZSM-5, between 10 and 20% by weight of an ultra-stable Y-type zeolite, between 20 and 30% by weight of a pseudoboehmite alumina, and between 20 and 40% by weight of kaolin. The phosphorous modified sub-micron ZSM-5 has an average crystal size between 50 and 400 nm, inclusive, and a silica to alumina ratio of 1:2 to 1:4, inclusive.

14 Claims, 3 Drawing Sheets

(56) References Cited

U.S. PATENT DOCUMENTS

| | | |
|---|---|---|
| 4,419,221 A | 12/1983 | Castagnos et al. |
| 4,826,793 A | 5/1989 | Velten et al. |
| 4,828,679 A | 5/1989 | Cormier, Jr. et al. |
| 4,980,053 A | 12/1990 | Li et al. |
| 5,326,465 A | 7/1994 | Yongqing et al. |
| 5,358,918 A | 10/1994 | Yukang et al. |
| 5,366,948 A | 11/1994 | Absil et al. |
| 5,456,821 A | 10/1995 | Absil et al. |
| 5,462,652 A | 10/1995 | Wegerer |
| 5,472,594 A | 12/1995 | Tsang et al. |
| 5,589,139 A * | 12/1996 | Zinke .................. C10G 11/182 208/113 |
| 5,888,378 A | 3/1999 | Kowalski |
| 6,211,104 B1 | 4/2001 | Shi et al. |
| 6,342,153 B1 | 1/2002 | Guan et al. |
| 6,566,293 B1 | 5/2003 | Vogt et al. |
| 6,656,346 B2 | 12/2003 | Ino et al. |
| 6,858,556 B2 | 2/2005 | Kuvettu et al. |
| 6,908,544 B2 | 6/2005 | Yu et al. |
| 7,456,123 B2 | 11/2008 | Wachter |
| 7,582,202 B2 | 9/2009 | Jones et al. |
| 7,727,924 B2 | 6/2010 | Liu et al. |
| 7,960,307 B2 | 6/2011 | Gao et al. |
| 2002/0189973 A1 | 12/2002 | Henry et al. |
| 2006/0060504 A1 | 3/2006 | Vierheilig |
| 2007/0060780 A1 | 3/2007 | Stamires et al. |
| 2008/0015105 A1 | 1/2008 | Lau et al. |
| 2008/0058197 A1 | 3/2008 | Liu et al. |
| 2008/0093263 A1 | 4/2008 | Cheng et al. |
| 2009/0134065 A1 | 5/2009 | Cheng et al. |
| 2009/0216058 A1 | 8/2009 | Dath et al. |
| 2009/0264693 A1 | 10/2009 | Xie et al. |
| 2010/0076227 A1 | 3/2010 | Li et al. |
| 2011/0118107 A1 | 5/2011 | Garcia-Martinez et al. |
| 2011/0207984 A1 | 8/2011 | Almeida et al. |
| 2013/0005565 A1 | 1/2013 | Shu et al. |

OTHER PUBLICATIONS

International Search Report with Written Opinion issued in related PCT Patent Application PCT/US2013/042413; dated Sep. 2, 2013; 16 pages.

Office Action issued in related Chinese Patent Application 2013800274359; dated Nov. 3, 2015; 9 pages.

Office Action issued in related Japanese Patent Application 2015514179; dated Nov. 26, 2015; 7 pages.

Written Opinion as issued in related Singapore Patent Application 11201407659X; dated Jul. 15, 2015; 10 pages.

* cited by examiner

METHOD FOR THE FLUIDIZED CATALYTIC CRACKING OF A HEAVY HYDROCARBON FEEDSTOCK

RELATED APPLICATIONS

This application is a continuation of and claims priority to U.S. patent application Ser. No. 13/900,725, titled "CATALYST FOR ENHANCED PROPYLENE IN FLUIDIZED CATALYTIC CRACKING" and filed on May 23, 2013, which claims priority to U.S. Provisional Patent Application No. 61/652,019, having the same title and filed on May 25, 2012, each of which is incorporated by reference in its entirety for the purposes of United States patent practice.

BACKGROUND

Field of the Invention

This invention relates to a method for the fluidized catalytic cracking (FCC) of a heavy hydrocarbon feedstock for improved production of light olefins. More specifically, this invention relates to a method for the FCC of a heavy hydrocarbon feedstock for the enhanced production of light olefins, particularly propylene, gasoline, and diesel.

Description of Related Art

Conventionally, to produce useful chemicals heavy hydrocarbon fractions, such as vacuum gas oil (VGO), are catalytically cracked with a catalyst in a fluidized cracking process. During this process, the catalyst typically circulates between a catalytic reactor and regenerator. In the catalytic reactor, hydrocarbons come in contact with hot catalysts that have been supplied from the regenerator and the hydrocarbons are cracked to produce gasoline, LPG, and dry gas. Coke is also produced during this process and is deposited on the catalyst. The cracked products are typically then separated from the coked catalyst in cyclone separators. Volatiles are stripped with steam and the coked catalyst is then sent to the regenerator. Regenerated catalyst particles are then recirculated to the reactor.

The product slate from conventional FCC process primarily consists of gasoline, in addition to light olefins, dry gas and LPG. Light olefins, particularly propylene, are increasingly gaining importance to refiners, as these products can increase refinery profit margins due to their high value. Propylene, which is used in the manufacture of various synthetic materials, particularly materials that are used in food packaging industry and thermoplastics, is in high demand. Additional demand for propylene exists in the area of alkylate production, which is increasingly being used as an additive for high-octane gasoline, due to environmental concerns raised by the use of olefins-containing FCC gasoline and aromatics-containing catalytically reformed gasoline. Propylene and butylene are the raw materials for the alkylate additive.

Small pore zeolites from the pentasil zeolite family, such as ZSM-5, have been previously used as catalysts in FCC operations. Additionally, pentasil zeolites have been used as additives in traditional FCC catalysts for the purpose of increasing light olefin yields. Prior art methods, however, suffer from the production of low yields of useful and desired light olefins. Thus, due to the various uses for light olefins, such as propylene, there exists a need for increased production and/or improved efficiency in the production of propylene.

SUMMARY

Embodiments of the invention provide a method for the fluid catalytic cracking of a heavy hydrocarbon feedstock. According to at least one embodiment, the method includes supplying the heavy hydrocarbon feedstock to a reaction zone having a catalyst, such that both the heavy hydrocarbon feedstock and the catalyst are in contact in a down-flow mode, wherein said contact between the heavy hydrocarbon feedstock and the catalyst takes place in a fluidized catalytic cracking apparatus having a separation zone, a stripping zone, and a regeneration zone. The method further includes maintaining the reaction zone at a temperature of between 500 and 600° C., such that the hydrocarbon feedstock converts into a cracked hydrocarbon effluent comprising light olefins, gasoline, and diesel. The catalyst includes between 10 and 20% by weight of a phosphorous modified sub-micron ZSM-5, between 10 and 20% by weight of an ultra-stable Y-type zeolite, between 20 and 30% by weight of a pseudoboehmite alumina, and between 20 and 40% by weight of kaolin. The phosphorous modified sub-micron ZSM-5 has an average crystal size between 50 and 400 nm, inclusive, and a silica to alumina ratio of 1:2 to 1:4, inclusive.

In another embodiment, the phosphorous modified sub-micron ZSM-5 includes phosphorous in a range of 5 to 10% by weight of the phosphorous modified sub-micron ZSM-5.

In another embodiment, the heavy hydrocarbon feedstock is one of a hydrotreated or un-hydrotreated VGO.

In another embodiment, the method further includes regenerating deactivated catalyst at a temperature of at least 700° C. using a source of oxygen and supplying the deactivated catalyst to the reaction zone.

In another embodiment, an amount of the oxygen introduced to the regeneration zone is such that a carbon-to-oxygen ratio is 2:5.

In another embodiment, the temperature in the reaction zone is maintained such that light olefins of the cracked hydrocarbon effluent includes $C_2$-$C_4$ olefins.

In another embodiment, a yield of $C_2$-$C_4$ olefins of the cracked hydrocarbon effluent is greater than 20% by weight.

In another embodiment, a combined yield of propylene and ethylene is greater than a yield of butenes in the cracked hydrocarbon effluent.

In another embodiment, a yield by weight of propylene is greater than a yield by weight of butenes in the cracked hydrocarbon effluent.

In another embodiment, a yield of propylene is greater than 14% by weight.

In another embodiment, a yield of gasoline is greater than 30% by weight.

In another embodiment, the gasoline has a GC-RON value greater than 88.

In another embodiment, the light olefins content of the gasoline has a value less than 20% by weight.

DETAILED DESCRIPTION

Although the following detailed description contains many specific details for purposes of illustration, it is understood that one of ordinary skill in the art will appreciate that many examples, variations and alterations to the catalyst and methods described herein are within the scope and spirit of the invention. Accordingly, the exemplary embodiments of the invention described herein are set forth without any loss of generality, and without imposing limitations, on the claimed invention.

As noted above, in certain embodiments of the present invention, a catalyst composition is provided for enhanced propylene production in a fluid catalytic cracking (FCC) process. In certain embodiments, a catalyst composition is provided for increased propylene and gasoline production from a heavy hydrocarbon stream.

In one aspect, the present invention is directed to FCC catalysts having both ultra-stable Y-type zeolite and pentasil zeolite as active catalyst components. These FCC catalysts contain both the ultra-stable Y-type zeolite and pentasil zeolite in a shaped particle. These FCC catalysts share the same matrix. In a preferred embodiment, each particle contains both the ultra-stable Y-type zeolite and the pentasil zeolite generally having a spherical shape.

In one embodiment of the present invention, FCC catalyst for enhanced production of light olefins from heavy hydrocarbon feedstock includes an ultra-stable Y-type zeolite, a pentasil zeolite, a binder material, and a clay filler material. In certain embodiments, FCC catalyst includes ultra-stable Y-type zeolite, pentasil zeolite, binder material, and clay filler. All percentages by weight refer to the weight of the entire FCC catalyst.

Ultra-stable Y-type zeolites contain greater ratios of silicon to aluminum than conventional Y-type zeolites. In certain embodiments, the ultra-stable Y-type zeolite acts as a cracking component. In certain embodiments, the ultra-stable Y-type zeolite does not include a rare earth element. In certain embodiments, the ultra-stable Y-type zeolite contains less than 0.2% by weight of a rare earth element, alternately between about 0.1 and 0.2% by weight, alternately between about 0.05 and 0.1% by weight. In certain embodiments, the ultra-stable Y-type zeolite is severely dealuminated. The percentage of ultra-stable Y-type zeolite present in FCC catalyst composition includes, for example, between about 10 and 30% by weight, alternately between about 10 and 20% by weight, alternately between about 15 and 25% by weight. In preferred embodiments the ultra-stable Y-type zeolite has a unit cell size of about 24.56 angstroms.

Figure 1:
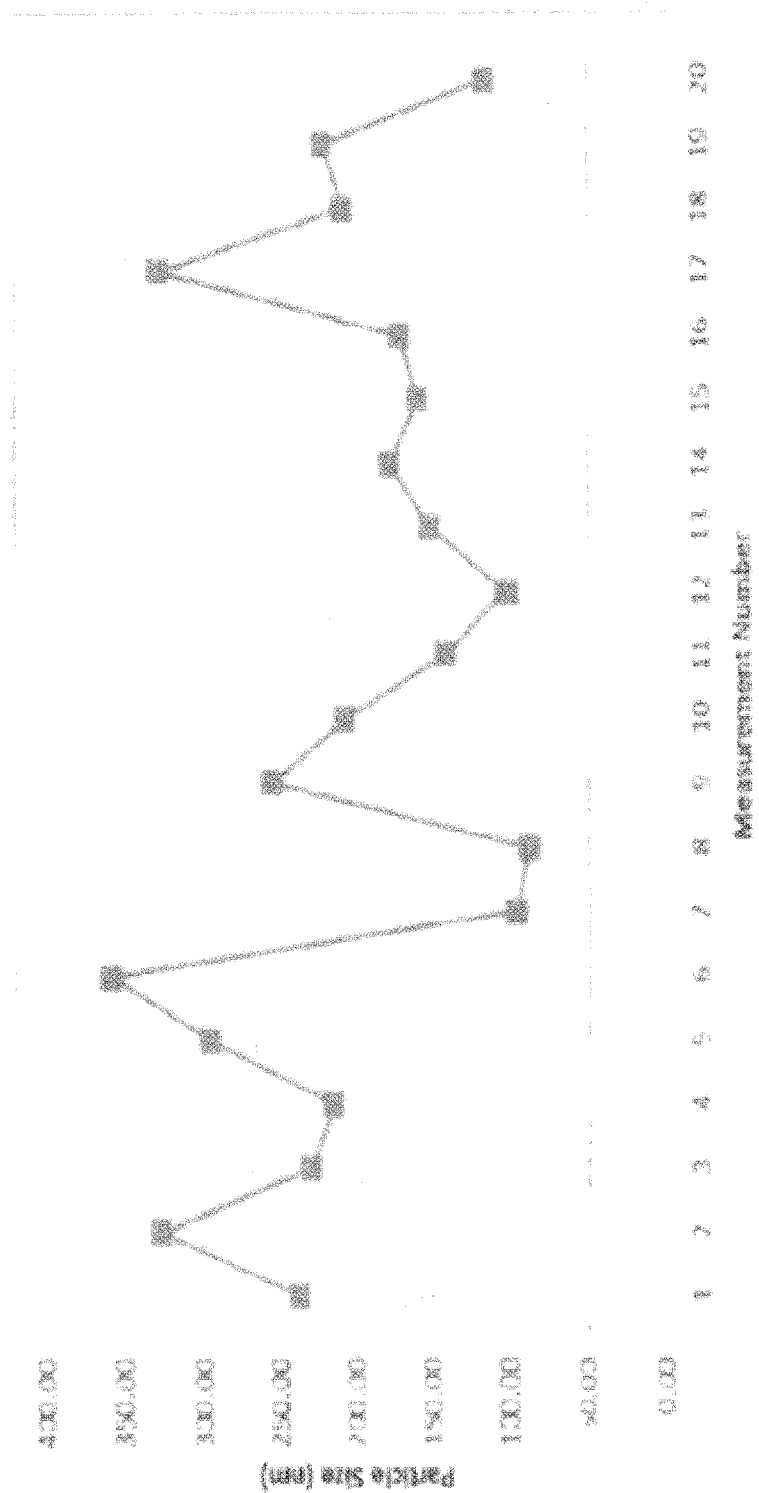
FIG. 1 shows the particle size distribution of a sub-micron ZSM-5 sample.
Figure 2:
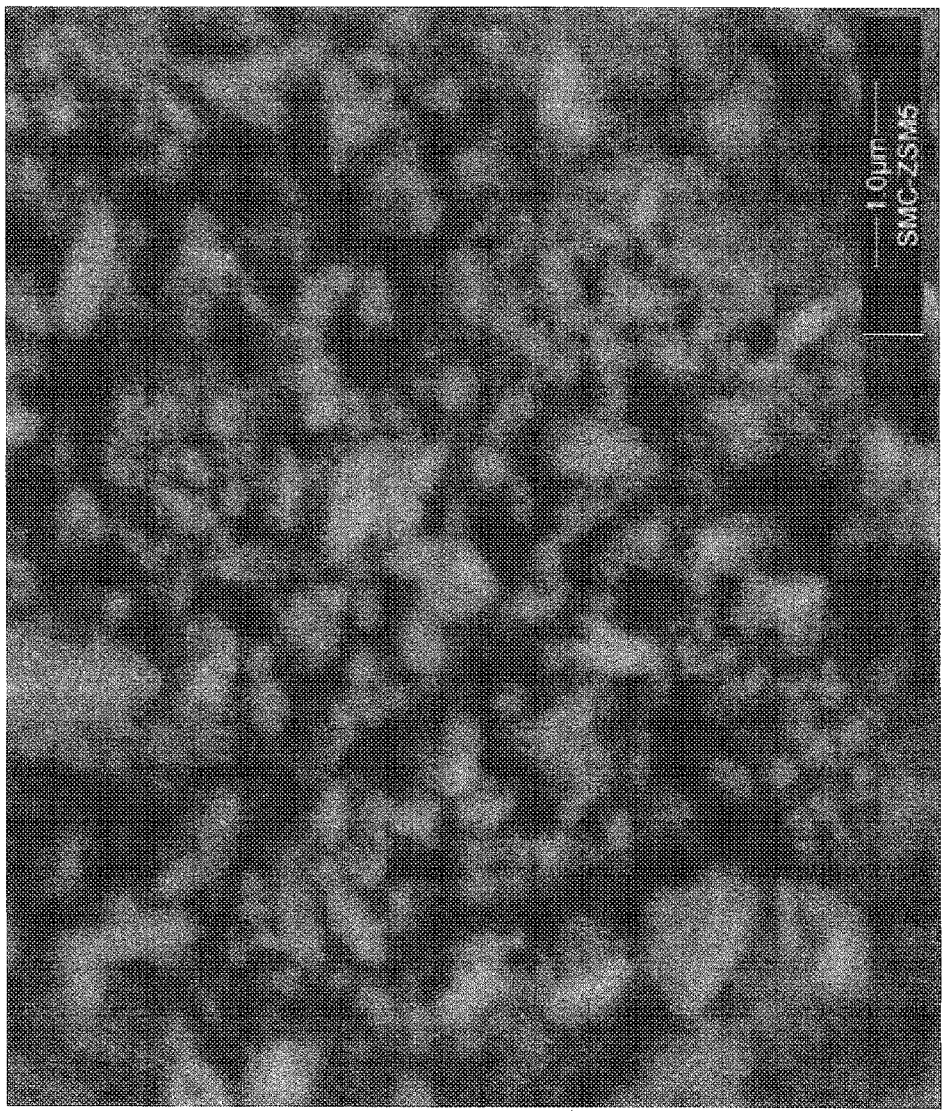
FIG. 2 shows the morphology of a sub-micron ZSM-5 sample as measured by ESEM.

In accordance with at least one embodiment of the present invention, FCC catalyst includes a pentasil zeolite. In preferred embodiments, FCC catalyst includes the pentasil zeolite ZSM-5. In the invention, the pentasil zeolite has a sub-micron crystal size. As used herein, the term "sub-micron" refers to a crystal size of the pentasil zeolite having an average particle size distribution below 4000 nm (below 4.0 microns), as shown in FIG. 1. In certain embodiments, FCC catalyst includes a pentasil zeolite having a sub-micron crystal size of between about 0.05 micron and 3 micron. In certain embodiments, the crystal size of the sub-micron ZSM-5 has an average particle size distribution of between about 0.05 and 0.4 microns. One standard morphology of the sub-micron ZSM-5 material is shown in FIG. 2. In certain preferred embodiments, the pentasil zeolite size is less than about 2 microns, alternately less than about 1 micron, alternately less than about 0.40 microns, alternately between about 0.40 microns and about 0.05 microns, alternately between about 0.35 microns and about 0.10 microns. The sub-micron size of the pentasil zeolite increases diffusion of the pentasil zeolite within FCC catalyst. In certain embodiments, the sub-micron ZSM-5 overcomes a diffusion limitation present in catalysts with larger ZSM-5 crystals. In certain embodiments, the pentasil zeolite, for example, sub-micron ZSM-5, includes a silica to alumina molar ratio of about 1:4, alternately about 1:3, and alternately about 1:2. In certain embodiments, the silica to alumina molar ratio can be between about 1:4 and 1:3; alternately between about 1:3 and 1:2; alternately between about 1:4 and 1:2. The concentration of pentasil zeolite, for example, sub-micron ZSM-5, in FCC catalyst can be between about 10 and 30% by weight, alternately between about 10 and 20% by weight, alternately between about 15 and 25% by weight.

In certain embodiments, the pentasil zeolite, for example, sub-micron ZSM-5, can be treated with phosphorous-containing compounds, for example, phosphoric acid or monoammonium phosphate, to produce phosphorous modified sub-micron ZSM-5. In certain embodiments, the total phosphorous concentration, present as $P_2O_5$, of the pentasil zeolite can be between about 5-20% by weight of ZSM-5, alternately between about 5-10% by weight of ZSM-5, alternately between about 10-20% by weight of ZSM-5. The phosphorous-containing compounds are used to stabilize the ZSM-5. No promoter is necessary or used.

The FCC catalyst useful in this invention is in an absence of any promoter, including acid promoters, solid acid promoters, clay promoters, or otherwise. The FCC catalyst may include an acid component, but the component does not act as a promoter. Instead, it provides some other function, such as stabilization of the catalyst. The FCC catalyst is also used in the absence of an acid dispersed alumina.

In certain embodiments, FCC catalyst includes a binder material. In certain embodiments, the binder material includes an alumina material. In at least one embodiment, the alumina material is pseudoboehmite. Pseudoboehmite is an alumina oxide hydroxide having a higher water concentration than boehmite. In certain embodiments, pseudoboehmite can be "Catapal" grade pseudoboehmite. In certain embodiments, the percentage of alumina in the composition can be between about 10 and 30% by weight, alternately between about 15 and 25% by weight, alternately between about 20 and 30% by weight.

In certain embodiments, the binder material, for example, an alumina material can optionally be peptized with a mono-protic acid, for example, $HNO_3$ or HCl. The peptized alumina material is believed to provide catalyst particles of enhanced physical strength. The peptized alumina enhance the binding, thereby improving the physical strength of FCC catalyst microspheres.

In certain embodiments, FCC catalyst includes a matrix can be an alumina containing material, such as a peptized pseudoboehmite, which can act as a binder.

In certain embodiments, FCC catalyst includes a clay filler material. In certain embodiments, the clay filler material includes a clay mineral. In at least one embodiment, the clay filler material includes kaolin. The FCC catalyst includes a clay filler material with an absence of pillared clay. The clay filler materials appropriate for use in the FCC catalyst of the invention do not act as a promoter. In certain embodiments, the percentage of clay filler material includes between about 20 and 50% by weight, alternately between about 20 and 40% by weight, alternately between about 35 and 45% by weight, alternately between about 40 and 50% by weight.

In other embodiments, FCC catalyst includes ingredients that are typically utilized for such compositions, such as alumina, silica, silica-alumina, titania, zirconia, clays, binders, and the like. The FCC catalyst is prepared and used in an absence of colloidal silica. In alternate embodiments, the catalyst composition can include other metal compounds, such as metal oxides, silicon oxide or aluminum oxide, metal hydroxides, and the like. In certain embodiments, FCC catalyst can be advantageously combined to form a shaped particle, such as a microsphere. In certain embodiments, the catalyst composition can be shaped into a shaped particle, such as a microsphere, and used in an FCC process, resulting in an increased propylene yield.

Figure 3:
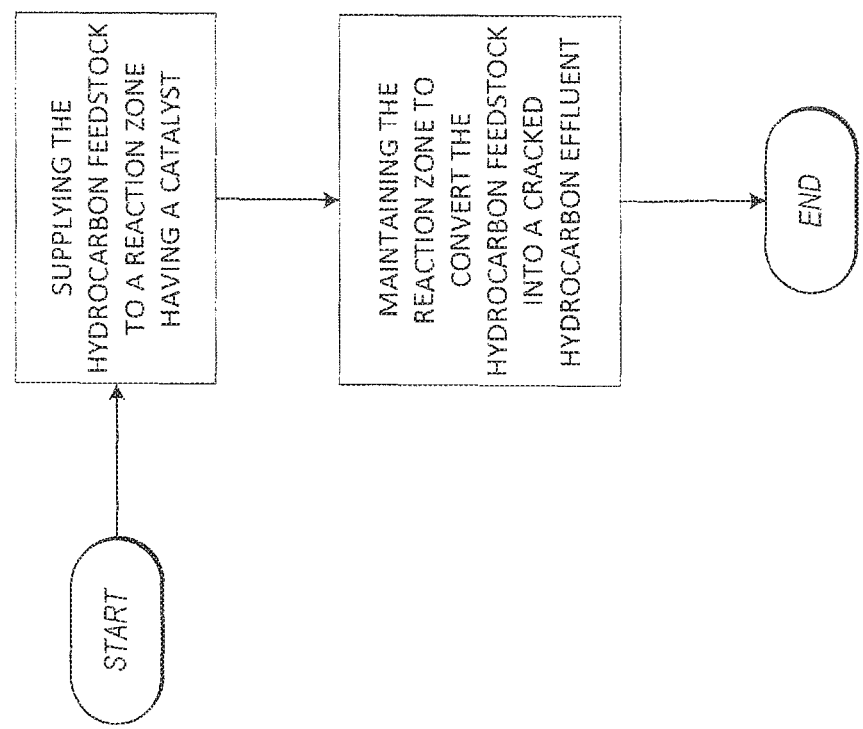
FIG. 3 shows a flow diagram of a method for the fluid catalytic cracking of a heavy hydrocarbon feedstock, according to an embodiment of the invention.

In one embodiment, there is provided a method, as shown in FIG. 3, including supplying the heavy hydrocarbon feedstock to a reaction zone having a catalyst, such that both the heavy hydrocarbon feedstock and the catalyst are in contact in a down-flow mode, wherein said contact between the heavy hydrocarbon feedstock and the catalyst takes place in a fluidized catalytic cracking apparatus having a separation zone, a stripping zone, and a regeneration zone. The method further includes maintaining the reaction zone at a temperature of between 500 and 600° C., such that the hydrocarbon feedstock converts into a cracked hydrocarbon effluent comprising light olefins, gasoline, and diesel. The catalyst includes between 10 and 20% by weight of a phosphorous modified sub-micron ZSM-5, between 10 and 20% by weight of an ultra-stable Y-type zeolite, between 20 and 30% by weight of a pseudoboehmite alumina, and between 20 and 40% by weight of kaolin. The phosphorous modified sub-micron ZSM-5 has an average crystal size between 50 and 400 nm, inclusive, and a silica to alumina ratio of 1:2 to 1:4, inclusive.

In one embodiment, FCC catalyst for enhanced production of light olefins from heavy hydrocarbon feedstock is provided. FCC catalyst includes between about 10-30% by weight of an ultra-stable Y-type zeolite; between about 10-30% by weight of pentasil zeolite; between about 10-30% by weight of a binder material; and between about 30-50% by weight of a clay filler material. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of pentasil zeolite; between about 20-30% by weight of a binder material; and between about 30-40% by weight of a clay filler material. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of pentasil zeolite; between about 20-30% by weight of a binder material; and between about 30-40% by weight of a clay filler material. In the catalyst of the present formulation, the two zeolites can exist within the same catalyst particle and can share the same matrix.

In another embodiment, FCC catalyst enhanced production of light olefins from heavy hydrocarbon feedstock is provided. The catalyst includes between about 10-20% by weight of an ultra-stable Y-type zeolite; between about 10-20% by weight of sub-micron ZSM-5; between about 20-30% by weight of a binder material; and between about 30-40% by weight of a clay filler material. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of phosphorous modified sub-micron ZSM-5; between about 20-30% by weight of a binder material; and between about 30-40% by weight of a clay filler material. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of phosphorous modified sub-micron ZSM-5; between about 20-30% by weight of a pseudoboehmite alumina material; and between about 30-40% by weight of a clay filler material. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of phosphorous modified sub-micron ZSM-5; between about 20-30% by weight of a peptized pseudoboehmite alumina material; and between about 30-40% by weight of a clay filler material. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of phosphorous modified sub-micron ZSM-5; between about 20-30% by weight of a peptized pseudoboehmite alumina material; and between about 30-40% by weight of kaolin. In the catalyst of the present formulation, the two zeolites can exist within the same catalyst particle and can share the same matrix.

In another embodiment, FCC catalyst for enhanced production of light olefins from heavy hydrocarbon feedstock is provided. The catalyst includes between about 10-20% by weight of an ultra-stable Y-type zeolite; between about 10-20% by weight of phosphorous modified sub-micron ZSM-5; between about 20-30% by weight of a peptized pseudoboehmite alumina material; and between about 20-40% by weight of kaolin. In the catalyst of the present formulation, the two zeolites can exist within the same catalyst particle and can share the same matrix.

In certain embodiments, the catalyst described herein can advantageously be used in a riser reaction vessel or a downer reaction vessel of an FCC process. The catalyst described herein can be used in a high temperature, high severity FCC process. Use of the catalyst described herein in a high temperature, high severity FCC process advantageously minimizes contact time to prevent saturation of the hydrocarbons, while cracking hydrocarbons. As used herein, high severity indicates a high catalyst to feed ratio. The advantage of the high temperature, high severity FCC process is to maximize conversion to propylene. It is understood that one of skill in the art can adapt the described catalyst particles for various types of reaction vessels.

In certain embodiments, the FCC catalyst described herein can be used in a high severity downer type FCC apparatus.

EXAMPLES

An FCC process involves a large number of variables and competing reactions. The large number of variables impacts the ability to predict the results based on a change in any one variable and means that a variable of the process cannot be looked at in a vacuum. In addition, the reactions of the catalytic cracking of mixed hydrocarbons cannot be considered in a vacuum because there are competing reactions not only between the many various components, but also between paths such as cracking and saturation reactions. In short, the degree of unknown makes accurate simulation of such processes impossible and the effect of proposed changes to the process unpredictable. Attempts to accurately simulate the reaction product mixture of an FCC process using the FCC catalyst described herein could not account for the numerous variables in components, and competing reactions. The following examples were necessary to understand the impact of using the FCC catalyst described herein.

In an FCC process, cracking and saturation are competing reaction paths. The extent of diffusion and the hydrogen transfer reaction depends to some degree on the contact time of the various reaction components and whether the reaction tends toward saturated or unsaturated reaction products.

Catalyst Preparation Example: ZSM-5 zeolite was impregnated with a solution of mono-ammonium phosphate, as described by Corma, et al. (Journal of Catalysis, 237 (2006) 267-277). The ZSM-5 powder was slurried in a solution of mono-ammonium phosphate, such that the percentage of solids in the slurry was approximately 10% by weight, and the amount of phosphorous in the solution was approximately 10% by weight, as based on the dry weight of the ZSM-5 zeolite. The slurry was heated with stirring at about 85° C. and evaporated to dryness. The resulting material was further dried at about 100° C. for two hours, and then calcined at about 500° C. for one hour to produce a phosphorous modified ZSM-5 zeolite, referred to as P-ZSM-5.

An FCC catalyst was prepared by blending 60 g (dry basis) P-ZSM-5 and 30 g (dry basis) ultra-stable Y-type zeolite (USY) with 410 g distilled water for two minutes to produce a zeolite slurry. To this zeolite slurry, 150 g (dry basis) kaolin clay powder was added, and the resulting slurry blended for five minutes.

Separately, a slurry of Catapal alumina was prepared by mixing 60 g (dry basis) Catapal alumina with 320 g distilled water. The slurry was peptized by adding 7.6 g concentrated nitric acid (70% by weight) and stirring for thirty minutes. The resulting peptized Catapal slurry was then added to the zeolite-kaolin slurry and blended for ten minutes to produce a viscous slurry wherein the individual catalyst particles remained suspended in the solution.

The resulting viscous slurry was dried at about 125° C., then granulated and sieved. The granules that passed through an 18 mesh screen (1000 microns) and were retained on a 20 mesh screen (841 microns) were calcined, steam deactivated, and tested in a microactivity (MAT) test. The catalyst product produced approximately 20% by weight propylene. The sieved catalyst was then steamed at 810° C. for approximately 6 hours in 100% steam. The resulting steamed catalyst was then tested in MAT according to ASTM method.

Example 1

Three samples were prepared according to the above procedure using different ZSM-5 crystal sizes, large crystal (LC), small crystal (SC), and the sub-micron crystal (SMC) of the invention. These catalysts were then tested in a fixed-bed microactivity testing unit using hyrotreated vacuum gas oil (VGO) at 575° C. and carbon-to-oxygen (C/O) ratios of 2:5. Table 1 lists the composition of each catalyst. Table 2 lists the product yields obtained for these catalysts determined at a constant conversion of 75%. The results illustrate that the catalyst containing SMC type ZSM-5 yields the greatest amount of $C_2$-$C_4$ olefins, particularly propylene and ethylene. That the catalyst of the invention should provide a result better than previous catalysts was surprising, given the large number of factors and competing reactions in this system. Attempts to accurately simulate the reaction product mixture of the FCC process using the FCC catalyst described herein could not account for the numerous variables in components, and competing reactions. The results in Table 2 show that the invention advantageously optimizes propylene production, although butenes decrease.

TABLE 1

| Catalyst Code | ZSM-5 Type | ZSM-5 Weight % | USY Weight % | Alumina Weight % | Kaolin Weight % |
|---|---|---|---|---|---|
| Cat. 1 | LC | 30 | 10 | 20 | 40 |
| Cat. 2 | SC | 30 | 10 | 20 | 40 |
| Cat. 3 | SMC | 30 | 10 | 20 | 40 |

TABLE 2

| Compound | Cat. 1 | Cat. 2 | Cat. 3 |
|---|---|---|---|
| | | Yields, weight % | |
| Ethylenes ($C_2$) | 2.5 | 2.9 | 3.1 |
| Propylenes ($C_3$) | 12.0 | 14.0 | 14.8 |
| Butenes ($C_4$) | 11.5 | 13.1 | 12.7 |
| $C_2$-$C_4$ Olefins | 26.1 | 30.0 | 30.5 |
| $H_2$ | 0.32 | 0.27 | 0.20 |
| $C_1$ | 1.4 | 1.4 | 1.2 |
| $C_2$ | 1.2 | 1.1 | 1.2 |
| $C_3$ | 1.3 | 1.2 | 1.2 |
| $iC_4$ | 2.5 | 2.6 | 3.1 |
| $nC_4$ | 0.59 | 0.64 | 0.61 |
| Groups | | | |
| Dry Gas | 5.4 | 5.7 | 5.6 |
| LPG | 27.9 | 31.5 | 32.4 |
| Gasoline | 38.8 | 34.9 | 33.0 |
| LCO + HCO | 24.8 | 27.9 | 25.2 |
| Coke | 2.5 | 2.4 | 2.5 |

Example 2

Three samples were prepared according to the above procedure using the SMC ZSM-5 zeolite. The SMC ZSM-5 zeolite was treated with different levels of phosphorous (P). The resulting catalysts were then tested in a fixed-bed MAT unit using hydrotreated VGO at 575° C. and C/O ratios of 2:5. Table 3 lists the composition of these catalysts. Table 4 lists the product yields obtained for these catalysts, as determined at a constant conversion of 75%. Attempts to accurately simulate the reaction product mixture of the FCC process using the FCC catalyst described herein could not account for the numerous variables in components, and competing reactions. The results generally demonstrate that maximum propylene and ethylene yields are achieved with low level phosphorous treatment, which advantageously also produces decreased amounts of coke.

TABLE 3

| Catalyst Code | SMC ZSM-5 P level | USY Weight % | Alumina Weight % | Kaolin Weight % |
|---|---|---|---|---|
| | Weight % | | | |
| Cat. 4 | 0 | 30 | 10 | 20 | 40 |
| Cat. 5 | Low | 30 | 10 | 20 | 40 |
| Cat. 6 | High | 30 | 10 | 20 | 40 |

TABLE 4

| Compound | Cat. 4 | Cat. 5 | Cat. 6 |
|---|---|---|---|
| | Yields, weight % | | |
| Ethylenes ($C_2$) | 3 | 4.1 | 3.5 |
| Propylenes ($C_3$) | 14.8 | 15.8 | 15.2 |
| Butenes ($C_4$) | 12.7 | 12.8 | 12.7 |
| $C_2$-$C_4$ Olefins | 30.5 | 32.7 | 31.4 |
| $H_2$ | 0.19 | 0.16 | 0.20 |
| $C_1$ | 1.3 | 1.2 | 1.5 |
| $C_2$ | 1.2 | 1.1 | 1.4 |
| $C_3$ | 1.3 | 1.2 | 1.2 |
| $iC_4$ | 3.0 | 3.2 | 2.1 |
| $nC_4$ | 0.60 | 0.46 | 1.1 |
| Groups | | | |
| Dry Gas | 5.6 | 6.6 | 6.6 |
| LPG | 32.4 | 33.5 | 32.3 |
| Gasoline | 33.5 | 31.6 | 34.6 |
| LCO + HCO | 4.3 | 4.4 | 3.3 |
| Coke | 2.7 | 1.4 | 1.7 |

Example 3

Two samples were prepared according to the above procedure to determine the effect of the ultra-stable Y-type (USY) zeolite concentration. The samples included 10% by weight and 20% by weight USY zeolite along with SMC ZSM-5. The resulting catalysts were then tested in a fixed-bed MAT unit using hyrotreated VGO at 575° C. and C/O ratios of 2:5. Table 5 provides the composition of these catalysts. Table 6 lists the product yields obtained for these catalysts, as determined at a constant conversion of 75%. Attempts to accurately simulate the reaction product mixture of the FCC process using the FCC catalyst described herein could not account for the numerous variables in components, and competing reactions. The results illustrate that lower USY zeolite concentration provides increased propylene and ethylene yields.

TABLE 5

| Catalyst Code | SMC ZSM-5 Weight % | USY Weight % | Alumina Weight % | Kaolin Weight % |
|---|---|---|---|---|
| Cat. 7 | 30 | 10 | 20 | 40 |
| Cat. 8 | 30 | 20 | 20 | 30 |

TABLE 6

| Compound | Cat. 7 | Cat. 8 |
|---|---|---|
| | Yields, weight % | |
| Ethylenes ($C_2$) | 3.11 | 2.87 |
| Propylenes ($C_3$) | 14.9 | 11.4 |
| Butenes ($C_4$) | 12.9 | 11.38 |
| $C_2$-$C_4$ Olefins | 30.91 | 25.65 |
| $H_2$ | 0.19 | 0.12 |
| $C_1$ | 1.26 | 1.38 |
| $C_2$ | 1.19 | 1.42 |
| $C_3$ | 1.32 | 0.95 |
| $iC_4$ | 3.02 | 1.9 |
| $nC_4$ | 0.6 | 0.4 |
| Groups | | |
| Dry Gas | 5.76 | 5.8 |
| LPG | 32.8 | 26.1 |
| Gasoline | 34.7 | 42.2 |
| LCO + HCO | 26 | 25 |
| Coke | 13.6 | 11.6 |

Example 4

In this example, the catalyst was prepared using an "alumina sol" process, which is a high solids, high viscosity process wherein the pseudobeohmite alumina acts an active binder for the catalyst. This is a route used to produce FCC catalysts. The catalyst of the present example was tested in a circulating catalyst pilot plant (CCPP) with a downer reactor at a temperature of 575° C. Hydrotreated VGO was supplied as the feedstock. The amount of catalyst used was about 5 kg, the feed oil rate was about 500 g/h, the reactor outlet temperature was maintained at about 575° C., the reaction pressure was 1 kg/cm²G, the regeneration temperature was maintained at about 720° C., and a 10% by weight dispersion steam was used. Table 7 lists the conversion and product yields obtained with the CCPP reactor. Attempts to accurately simulate the reaction product mixture of the FCC process using the FCC catalyst described herein could not account for the numerous variables in components, and competing reactions. These results show that the catalyst of present invention gives a propylene yield of up to about 21% by weight, at a C/O ratio of 41.0, and a gasoline yield of up to about 34% by weight.

TABLE 7

Conversion and Product Yields (CCPP, 575° C.).

| Catalyst ID | MB3-13 SD | MB3-13 SD | MB3-13 SD |
|---|---|---|---|
| C/O ratio | 16.5 | 24.8 | 41.2 |
| Conversion % | 78.4 | 84.2 | 86.7 |
| Compounds | Yields, weight % | | |
| Ethylenes ($C_2$) | 2.6 | 2.6 | 3.1 |
| Propylenes ($C_3$) | 16.0 | 17.9 | 20.8 |
| Butenes ($C_4$) | 15.4 | 17.1 | 17.9 |
| $C_2$-$C_4$ Olefins | 34.0 | 37.6 | 41.8 |
| $H_2$ | 0.1 | 0.1 | 0.1 |
| $C_1$ | 1.4 | 1.0 | 1.0 |
| $C_2$ | 1.1 | 0.7 | 0.6 |
| $C_3$ | 0.90 | 1.03 | 1.33 |
| $iC_4$ | 1.5 | 2.1 | 3.1 |
| $nC_4$ | 0.4 | 0.6 | 0.8 |
| Groups | | | |
| Dry Gas | 5.2 | 4.4 | 4.9 |
| LPG | 34.1 | 38.8 | 43.9 |
| Gasoline | 35.7 | 37.5 | 34.4 |
| Light Cycle Oil (LCO) | 11.3 | 10.2 | 8.9 |
| Heavy Cycle Oil (HCO) | 10.3 | 5.6 | 4.4 |
| Coke | 0.9 | 1.2 | 1.6 |
| Total | 98 | 98 | 98 |

Example 5

VGO cracking was performed in the CCPP reactor described in Example 4 at temperatures ranging from 550° C. to 600° C. with a catalyst. Data obtained for cracking at temperatures of 550° C., 575° C. and 600° C. is listed in Table 8. Attempts to accurately simulate the reaction product mixture of the FCC process using the FCC catalyst described herein could not account for the numerous variables in components, and competing reactions. The data demonstrates that the catalyst can be used to crack VGO at temperatures that are similar to those that are presently used in conventional FCC processes.

TABLE 8

| Temperature, ° C. | 550° C. | 575° C. | 600° C. |
|---|---|---|---|
| C/O ratio | 38.7 | 41.2 | 41.7 |
| Conversion % | 86.4 | 86.7 | 87.3 |
| Compounds | Yields, weight % | | |
| Ethylenes ($C_2$) | 2.6 | 3.1 | 3.7 |
| Propylenes ($C_3$) | 19.6 | 20.8 | 21.6 |
| Butenes ($C_4$) | 17.5 | 18.0 | 22.2 |
| $C_2$-$C_4$ Olefins | 39.7 | 41.8 | 43.8 |
| $H_2$ | 0.1 | 0.1 | 0.1 |
| $C_1$ | 0.7 | 1.0 | 1.5 |
| $C_2$ | 0.5 | 0.6 | 0.9 |
| $C_3$ | 1.34 | 1.33 | 1.34 |
| $iC_4$ | 3.9 | 3.1 | 2.6 |
| $nC_4$ | 0.9 | 0.8 | 0.7 |
| Groups | | | |
| Dry Gas | 3.9 | 4.9 | 6.2 |
| LPG | 43.1 | 43.9 | 44.7 |
| Gasoline | 35.6 | 34.4 | 33.1 |
| Light Cycle Oil (LCO) | 9.3 | 8.9 | 8.4 |
| Heavy Cycle Oil (HCO) | 4.4 | 4.4 | 4.2 |
| Coke | 1.7 | 1.6 | 1.7 |
| Total | 97.9 | 98.1 | 98.4 |

Example 6

The performance of one embodiment of the catalyst of the present invention was compared with a mixture that includes a commercial FCC catalyst and an additive. Hydrotreated VGO was cracked at 600° C. in CCPP, at the conditions listed in Example 4. The results are provided in Table 9 and show that the catalyst provides greater yield of $C_4$ olefins, with comparable yields of $C_3$ olefins. Gasoline production with the catalyst described herein is greater than that of the commercial FCC catalyst and additive mixture, while coke production is approximately the same. Attempts to accurately simulate the reaction product mixture of the FCC process using the FCC catalyst described herein could not account for the numerous variables in components, and competing reactions.

TABLE 9

| Cat. ID | MB3-13 SD | Mix 75 |
|---|---|---|
| C/O ratio | 41.7 | 47.0 |
| Conversion % | 87.3 | 87.1 |
| Compounds | Yields, weight % | |
| Ethylenes ($C_2$) | 3.7 | 6.6 |
| Propylenes ($C_3$) | 21.6 | 22.1 |
| Butenes ($C_4$) | 19.3 | 16.5 |
| $C_2$-$C_4$ Olefins | | |
| $H_2$ | 0.1 | 0.1 |
| $C_1$ | 1.5 | 2.9 |
| $C_2$ | 0.9 | 1.9 |
| $C_3$ | 1.3 | 1.9 |
| $iC_4$ | 2.6 | 2.4 |
| $nC_4$ | 0.7 | 0.8 |
| Groups | | |
| Dry Gas | 6.2 | 11.4 |
| LPG | 45.6 | 43.5 |
| Gasoline | 33.1 | 29.9 |
| Light Cycle Oil (LCO) | 8.4 | 8.0 |
| Heavy Cycle Oil (HCO) | 4.2 | 4.9 |
| Coke | 1.7 | 1.7 |

Example 7

Gasoline composition of selected samples from pilot plant experiments was determined by GC-PIONA analysis. Table 10 lists this composition. Attempts to accurately simulate the reaction product mixture of the FCC process using the FCC catalyst described herein could not account for the numerous variables in components, and competing reactions.

TABLE 10

| Component | 550° C. | 575° C. |
|---|---|---|
| n paraffin | 3.8 | 5.3 |
| iso paraffin | 13.5 | 12.3 |
| Olefins | 19.3 | 12.3 |
| Naphthenes | 5.7 | 4.8 |
| Aromatics | 57.7 | 61.1 |
| Benzene | 1.9 | 2.1 |
| Toluene | 8.1 | 9.1 |
| p-xylene | 3.0 | 3.3 |
| m-xylene | 5.9 | 6.5 |
| o-Xylene | 3.0 | 3.3 |
| GC-RON | 88.6 | 89.2 |

The methods and compositions provided herein solve several problems that are frequently encountered Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an", and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value.

When such a range is expressed, it is to be understood that another embodiment is from the one particular value and/or to the other particular value, along with all combinations within said range. Similarly, when a range is expressed as "less than" a particular value, this indicates a value that is less than or equal to the particular value unless indicated otherwise by the context of the specification.

Throughout this application, where patents or publications are referenced, the disclosures of these references in their entireties are intended to be incorporated by reference into this application, in order to more fully describe the state of the art to which the invention pertains, except when these references contradict the statements made herein.

As used herein and in the appended claims, the words "comprise", "has", and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

That which is claimed is:

1. A method for the fluid catalytic cracking of a heavy hydrocarbon feedstock, the method comprising:
   supplying the heavy hydrocarbon feedstock to a reaction zone comprising a catalyst, such that both the heavy hydrocarbon feedstock and the catalyst are in contact in a down-flow mode, wherein said contact between the heavy hydrocarbon feedstock and the catalyst takes place in a fluidized catalytic cracking apparatus comprising a separation zone, a stripping zone, and a regeneration zone; and
   maintaining the reaction zone at a temperature of between 500 and 600° C., such that the hydrocarbon feedstock converts into a cracked hydrocarbon effluent comprising light olefins, gasoline, and diesel,
   wherein the catalyst comprises 30% by weight of a phosphorous modified sub-micron ZSM-5, 10% by weight of an ultra-stable Y-type zeolite, 20% by weight of a pseudoboehmite alumina, and 40% by weight of kaolin, and
   wherein the phosphorous modified sub-micron ZSM-5 has an average crystal size between 50 and 400 nm, inclusive, and a silica to alumina ratio of 1:2 to 1:4, inclusive.

2. The method of claim 1, wherein the reaction zone is a downer of a fluidized catalytic cracking unit.

3. The method of claim 1, wherein the phosphorous modified sub-micron ZSM-5 includes phosphorous in a range of 5 to 10% by weight of the phosphorous modified sub-micron ZSM-5.

4. The method of claim 1, wherein the heavy hydrocarbon feedstock comprises one of a hydrotreated or an un-hydrotreated VGO.

5. The method of claim 1, further comprising:
   regenerating deactivated catalyst at a temperature of at least 700° C. using a source of oxygen and supplying the deactivated catalyst to the reaction zone.

6. The method of claim 5, wherein an amount of the oxygen introduced to the regeneration zone is such that a carbon-to-oxygen ratio is 2:5.

7. The method of claim 1, wherein the temperature in the reaction zone is maintained such that light olefins of the cracked hydrocarbon effluent comprise $C_2$-$C_4$ olefins.

8. The method of claim 7, wherein a yield of $C_2$-$C_4$ olefins of the cracked hydrocarbon effluent is greater than 20% by weight.

9. The method of claim 7, wherein a combined yield of propylene and ethylene is greater than a yield of butenes in the cracked hydrocarbon effluent.

10. The method of claim 7, wherein a yield by weight of propylene is greater than a yield by weight of butenes in the cracked hydrocarbon effluent.

11. The method of claim 7, wherein a yield of propylene is greater than 14% by weight.

12. The method of claim 1, wherein a yield of gasoline is greater than 30% by weight.

13. The method of claim 12, wherein the gasoline has a GC-RON value greater than 88.

14. The method of claim 12, wherein the light olefins content of the gasoline has a value less than 20% by weight.

* * * * *